United States Patent [19]

Mulder

[11] Patent Number: 4,821,306

[45] Date of Patent: Apr. 11, 1989

[54] SYSTEM FOR DETECTING TWO X-RAY ENERGIES

[75] Inventor: Hendrik Mulder, Delft, Netherlands

[73] Assignee: B.V. Optische Industrie "De Oude Delft", Delft, Netherlands

[21] Appl. No.: 744,792

[22] Filed: Jun. 13, 1985

[30] Foreign Application Priority Data

Jun. 19, 1984 [NL] Netherlands .................. 8401946

[51] Int. Cl.$^4$ .............................................. G21K 3/00
[52] U.S. Cl. ..................................... 378/156; 378/146; 250/367; 250/505.1
[58] Field of Search .................... 378/5, 156–159, 378/146, 145, 19; 250/366–367, 505.1

[56] References Cited

U.S. PATENT DOCUMENTS

| | | | |
|---|---|---|---|
| 3,784,816 | 1/1974 | Abrahamsson | 358/111 |
| 3,944,822 | 3/1976 | Dzubay | 378/145 |
| 4,132,653 | 1/1979 | Samson | 378/70 |
| 4,132,895 | 1/1979 | Froggatt | 378/146 |
| 4,149,081 | 4/1979 | Seppi | 378/5 |
| 4,206,361 | 6/1980 | Hounsfield et al. | 250/366 |
| 4,247,774 | 1/1981 | Brooks | 250/367 |
| 4,255,664 | 3/1981 | Rutt et al. | 378/157 |
| 4,292,538 | 9/1981 | Carlson | 250/367 |
| 4,511,799 | 4/1985 | Bjorkholm | 378/5 |
| 4,626,688 | 12/1986 | Barnes | 378/156 |
| 4,675,893 | 6/1987 | Duinker et al. | 378/145 |
| 4,715,056 | 12/1987 | Vlasbloem et al. | 378/145 |

FOREIGN PATENT DOCUMENTS 0002777 1/1977 Japan .......................... 250/370 E

OTHER PUBLICATIONS

"NaI(Tl)-CsI(Na) Phoswich Detectors for X-Ray Astronomy", Kurfess et al., IEEE Transactions on Nuclear Science, vol. NS-22, 2-1975.

"The Preparation and Performance of Thin Vacuum-Deposited CsI(Na) Scintillation Layers", by Van Der Ven, Nuclear Instruments and Methods, vol. 75, #2, 1969.

"Definition and Measurement of Means of Filtered X-Radiation", by Grudskii et al., Pribory i Tekhnika Éksperimenta, #4, Jul.-Aug. 1974.

"A Differential Counter For X-Ray Structural Analysis", by Vasil'ev et al., Pribory i Tekhnika Éksperimenta, #5, Sep.-Oct. 1974.

Primary Examiner—Craig E. Church
Assistant Examiner—John C. Freeman
Attorney, Agent, or Firm—Louis E. Marn

[57] ABSTRACT

A system comprising an X-ray source (1), an elongate detector tube (3) including at least one cathode (5) extending in the longitudinal direction of the tube and at least one anode (6) located opposite to the cathode, a slit diaphragm (2), and a filter (4) mounted in the path between the X-ray source (1) and the detector tube (3). The filter (4) blocks relatively low energy X-radiation in a portion of the beam emitted by the source (1). The cathode (5) is provided with an X-ray detection layer consisting of two strips (8',8") extending in the longitudinal direction of the tube (3). One strip (8") receives the radiation passed by the filter (4) and the other strip (8') receives the unfiltered radiation. The one strip (8") is of considerably greater thickness than the other strip (8').

11 Claims, 2 Drawing Sheets

SYSTEM FOR DETECTING TWO X-RAY ENERGIES

The invention relates to a system comprising an X-ray source, an elongate detector tube and a slit diaphragm between the X-ray source and the detector tube, the slit-shaped aperture of the diaphragm extending parallel with the longitudinal axis of the detector tube and the detector tube including at least one cathode extending in the longitudinal direction of the tube and at least one anode located opposite to the cathode and likewise extending in the longitudinal direction of the tube, the tube being evacuated and, during operation, an electrical field being established between the cathode and the anode. Such an elongate X-ray detector tube is disclosed in Dutch patent application 79,00878 and is particularly suited for use in slit radiography.

It is known from the article "Computerized dual-energy imaging: a technical description" by J. Coumans et al in Medicamundi, Vol. 27, No. 3, 1982, to produce so-called dual-energy X-ray images by alternately operating an X-ray source at two different high voltage levels, for example 70 and 120 kVp. The alternate application of the two voltages to the X-ray source results in the generation of X-ray beams having mutually different "energetic centers of gravity", in other words, mutually different hardnesses. By successively irradiating the object to be examined, such as the body of a patient, with X-radiation having a first energetic center of gravity, and X-radiation having a second energetic center of gravity, it is possible to so process, for example by means of a computer, the resultant X-ray images that, for example, only tissue and no bones are imaged, permitting the imaging of tissue located behind, for example, ribs. This is the result of the fact that different materials in, for example, the human body exhibit different absorption to X-radiation of different hardnesses.

The use of different levels for the high voltage supply of an X-ray source entails the drawback that the irradiation has to be performed at two successive points of time, while the interval between these points of time must not be too long as otherwise movements of the object under examination can result in errors when processing the images obtained by means of the different X-ray beams.

In slit radiography, as described in, for example, U.S. patent application No. 06/648,707, filed on Sept. 7, 1984, mechanical scanning is required for obtaining a complete image of a patient, while the scanning time for a total image height of 0.4 m is approximately 1 second. This scanning time is so long that a subsequent second scan, at a different X-ray source voltage, inevitably leads to a changed geometry of the image of the patient, which is unacceptable.

It is an object of the invention to provide facilities permitting the application of the so-called dual energy image processing techniques to slit radiography, without the need for switching the anode voltage of the X-ray source.

To this end, in accordance with the invention in a system of the above type a filter is mounted near the slit diaphragm in the path between the X-ray source and the detector tube, which filter intercepts a portion of the X-ray beam emitted by the source over the entire length of the slit-shaped aperture and blocks relatively low energy X-radiation in this beam portion, and the cathode is provided with an X-ray detection layer consisting of two essentially parallel strips extending in the longitudinal direction of the tube, one of these strips receiving the radiation passed by the filter and the other of the strips receiving the unfiltered radiation. The one strip preferably is of considerably greater thickness than the other strip.

The invention is based on the insight that, in slit radiography, the local exposure time is considerably less than the canning time for the complete image. The local exposure time is the time required by a flat fan X-ray beam for passing a point of the patient. This beam is obtained by means of the slit diaphragm between the X-ray source and the patient, which diaphragm only allows X-radiation to be incident, after passing through the patient, on the detector tube within a spatial angle defined by the strip-like detector seen from the focal point of the X-ray source. When this slit diaphragm is thought to be divided into two narrower, superimposed slits of equal length, which slits need, in general, not be equally narrow, the original X-ray beam may be regarded to be composed of two superimposed, even flatter fan subbeams each incident on an associated narrow strip of the detector. The mechanical scanning thus results in two images, with a time difference of less than 0.1 second between the instants at which the same points of the patient are recorded. It is known that the radiation is hardened by placing a plate of suitable thickness of, for example, Pb or Cu in an X-ray beam, which means that lower energy radiation, i.e. radiation of lower frequencies, is attenuated to a higher degree than higher energy radiation, i.e. radiation of higher frequencies.

Matter acts as a high pass filter upon X-radiation passing therethrough. Low pass filters for X-radiation cannot be realized in actual practice.

In accordance with the invention, such a high pass filter is so mounted at the slit diaphragm in the X-ray beam path that it intercepts a portion of the flat fan X-ray beam, which portion actually constitutes one of the aforesaid subbeams. The passage of this subbeam through the filter results in a shift of the "energetic center of gravity" to a higher energy relative to that of the subbeam which passes through the slit diaphragm without being filtered. Furthermore, in accordance with a preferred embodiment of the invention the detector is so arranged that the strip on which the unfiltered beam is incident, predominantly absorbs soft radiation and optimally passes hard radiation while the strip on which the filtered beam is incident, optimally absorbs the radiation hardened by the filter. In this manner, the spacing between the "energetic centers of gravity" with which the beams act on the detector, can be increased even further.

To achieve the detector characteristics desired, the strip of the detector on which the filtered beam is incident, is of considerably greater thickness than the other strip. If the detector includes an X-ray screen, besides the thickness of the screen also the screen material of one strip can be selected to differ from that of the other strip. For example, screen material consisting of atoms of low atomic number will predominantly absorb soft radiation.

The invention will be described in greater detail hereinafter with reference to the accompanying drawing in which:

FIG. 1b shows an embodiment of the cathode in FIG. 1a.

Figure 4:
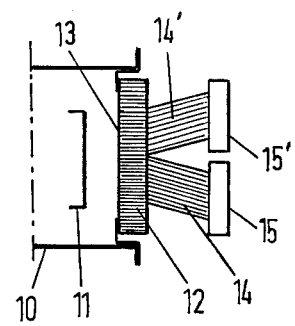
Figure 2:
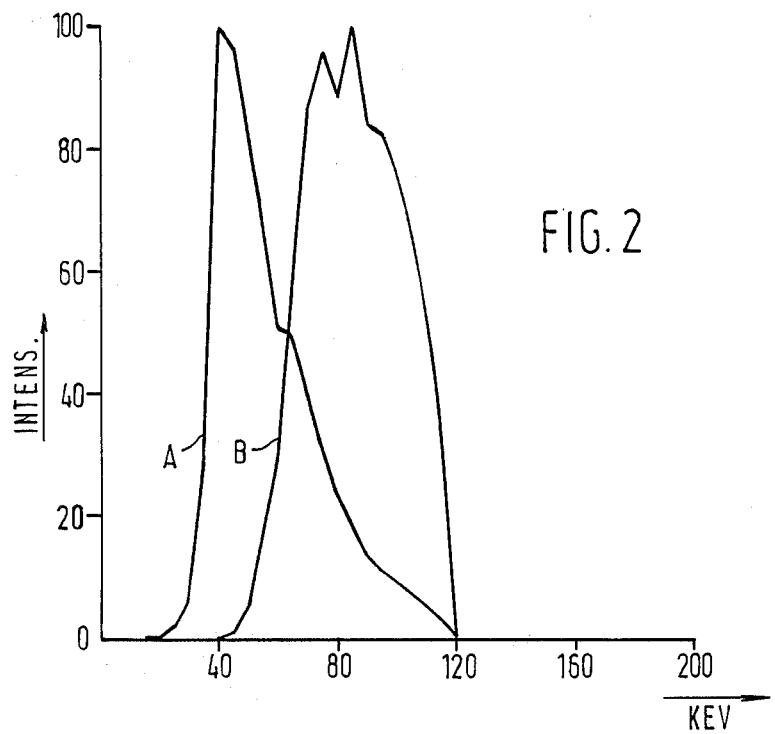
Figure 3:
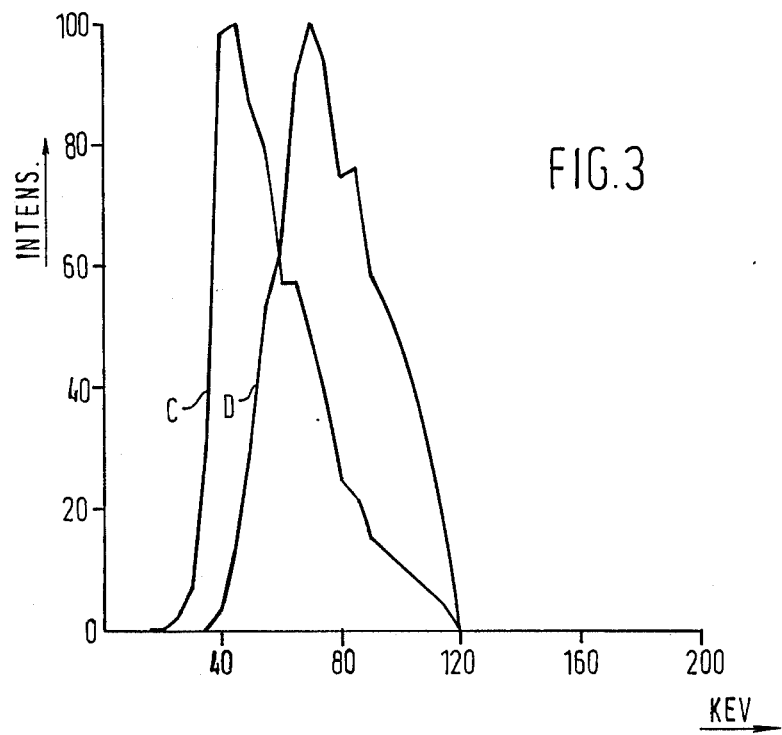

FIG. 2 graphically illustrates the relationship between the X-ray energy and the intensity in a first embodiment of a system according to the invention;

FIG. 3 graphically illustrates the relationship between the X-ray energy and the intensity in a second embodiment of a system according to the invention; and FIG. 4 schematically shows the structure of a different type of detector tube for a system according to the invention.

Figure 1:
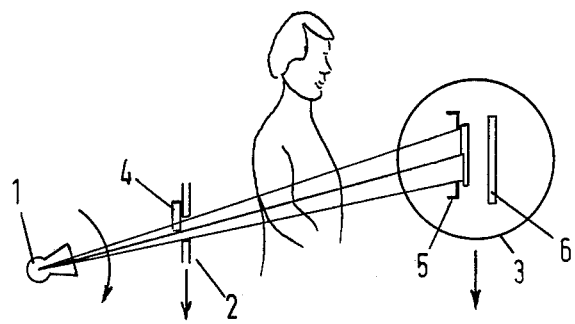
FIG. 1 shows a system for detecting X-radiation in accordance with the invention.
Figure 5:
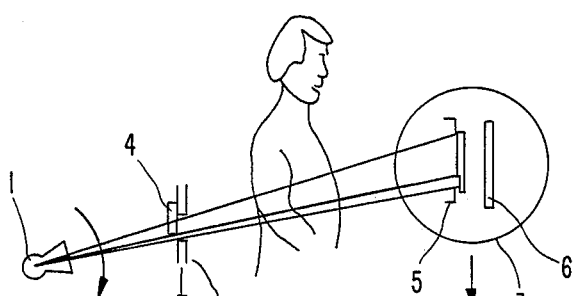
Figure 1B:
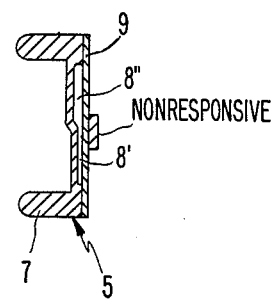

FIG. 5 shows a different embodiment of the system for detecting X-radiation shown in FIG. 1.

FIG. 1 shows a system for slit radiography embodying the ideas underlying the present invention. Reference numeral 1 designates a source emitting X-radiation, which radiation passes through a diaphragm 2 and the schematically shown body of a patient to be incident on an X-ray detector tube 3.

Source 1 is mounted for rotation about its axis, while diaphragm 2 and tube 3 are caused to perform a continuous, linear movement during the rotation of source 1 so that a portion of the body of the patient is irradiated by a fan X-ray beam extending normal to the plane of the drawing, with the radiation transmitted being incident on tube 3. Instead of performing a linear movement, the diaphragm may rotate about the axis of rotation of the source. For a more detailed explanation of the operation of the system shown, reference is made to U.S. patent application No. 06/648,707, filed on Sept. 7, 1984. In accordance with the invention, a filter 4 is mounted near diaphragm 2, which filter intercepts a portion of the beam emanating from source 1 to block the relatively soft X-radiation in this beam and pass the harder radiation. In principle, the filter may be of any material known to suit this purpose but materials such as copper or lead are preferred.

Tube 3 is evacuated and, during operation, an electrical field is established between cathode 5 and anode 6.

Figure 1A:
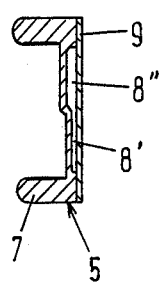
FIG. 1a shows an enlarged detail of FIG. 1.

In FIG. 1a, cathode 5 is shown on an enlarged scale and includes a cathode support 7 having its rear face coated with a layer 8', 8" of, for example, CsI. In layer 8', 8" the X-radiation is converted into a visible image, which image releases electrons in the photocathode 9 mounted on the rear face of layer 8', 8", which electrons are projected onto the anode and can there be converted in known per se manner into an intensified visible image. The strip-shaped portion 8' of the CsI layer is relatively thin and the strip-shaped portion 8" is of considerably greater thickness, while the system is so dimensioned that the radiation passed by filter 4, i.e. the hardened radiation, is incident on the thicker portion 8" of the CsI layer, so that an image essentially formed by hard X-radiation is formed on the rear face of strip 8". This image causes electrons to emanate from photocathode 9, which electrons are released by the relatively hard, high energy X-radiation.

The unfiltered radiation is incident on the thinner strip 8' of the cathode, in which strip predominantly the softer radiation is absorbed, so that in strip 8' an image is formed by the essentially soft X-radiation, whereby electrons are released in the photocathode, of which electrons the percentage caused by soft radiation is considerably higher than the percentage of electrons emanating from the rear face of strip 8" as a result of soft radiation.

The above will be elucidated with reference to FIGS. 2 and 3.

When determining the graphs of FIGS. 2 and 3, the X-ray source was operated at a constant voltage of 130 kVp and CsI was used as the detection material for layer 8', 8".

In FIG. 2, curve A is the product curve of the emission of the X-ray tube, the transmission of a patient (150 mm $H_2O$) and the absorption of a CsI layer 8' of 0.05 mm thickness, as a function of the keV value of the X-radiation. Curve B differs from curve A as the radiation is additionally filtered by filter 4, which filter consists of Cu of 2 mm thickness, and as absorption occurs in layer 8" of CsI, which layer has a thickness of 0.3 mm. Both curves are standardized at a peak value 100.

The "center of gravity" of curve A is at 57 keV and that of curve B at 85 keV. The light yield of the unfiltered, relatively soft radiation (A) is approximately 2.7 times higher than that of the filtered, relatively hard radiation (B). If this should present a problem when processing the images, the ratio of the widths of the beams and detector strips can be so modified by appropriately locating filter 4 and detector strips 8' and 8" correspondingly therewith, on which strips he respective X-ray beams are incident, that the period of time during which strip 8" is exposed to radiation exceeds the period of time during which strip 8' is exposed.

Also the curves C and D show the effect of filtering on the keV value of the X-radiation. Also these curves are standardized at a peak value 100. The difference between these curves and those shown in FIG. 2 is that the unfiltered radiation C is absorbed by a CsI layer 8' having a thickness of 0.1 mm instead of 0.05 mm, and that the filtered radiation is filtered by a Cu filter 4 having a thickness of 1 mm instead of 2 mm. The "center of gravity" of curve C is now at 58 keV and that of curve D at 78 keV. The distance between the "centers of gravity" has become smaller, mainly as a result of the lesser filtering. The light yield of the unfiltered radiation (C) is about 2 times higher than that of the filtered radiation (D) and about 1.8 times higher than the light yield obtained when using a CsI detection strip of 0.05 mm thickness, as this is done in the case of curve A.

If also a CsI detection strip of 0.3 mm thickness is used for the unfiltered radiation, the "center of gravity" will be at 61 keV and the light yield will be a good 4 times higher than that of the filtered radiation, as shown in curve D.

If a CsI detection strip of 1 mm thickness is used for the filtered radiation, the "center of gravity" will be at 88 keV and the light yield will be approximately twice as high as that obtained when using CsI of 0.3 mm thickness. However, for the present the manufacture of a CsI detection layer of 1 mm thickness presents insurmountable technological problems.

In the system according to the invention, the processing of the image formed by means of the detection layer 8', 8" should self-evidently be so performed that two images are produced, namely a first image corresponding with the upper part and a second image corresponding with the lower part of the image formed on the anode of the image intensifier tube. This can be realized in different manners.

The anode 6 may be composed of two strips 16 and 16' which are each of a different phosphor, so that the electrons emanating from the thicker section of the detector produce light of a color different from that produced by the electrons emanating from the thinner section. It is also possible to use one type of phosphor which is externally coated with two types of filtering material having mutually different spectral transmissivities. Furthermore, it is also possible to employ filters causing the polarization state of the light from the two strips to differ from each other.

The difference in color or polarization state renders it possible to split up the light path by means of color- or polarization-sensitive splitter mirrors to two detectors, films or so-called diode arrays. In the case of color information, it is also possible to directly record the information provided by the anode on color film without additional splitting.

Furthermore, a conventional anode may be used, in which case the light path can be split up by means of a splitter mirror for application through two parallel objectives to two diode arrays or two films. In the latter case, a shield or knife-edge travelling in front of the film should be employed to ensure that only one strip of the detector is imaged on each film.

Finally, the anode may be a glass fiber anode on which diode arrays are provided for scanning the different regions of the anode. This is schematically shown in FIG. 4, where reference numeral 10 designates an X-ray image intensifier tube including a cathode 11, for example of similar structure as cathode 5 of FIG. 1, and an anode 13 mounted on a glass fiber plate 12. Additional glass fiber plate elements 14 and 14' are mounted on glass fiber plate 12, which elements support diode arrays 15 and 15' at their ends remote from plate 12. In this arrangement of the anode, the structure disclosed in Dutch patent application No. 84,01105 may further be used to advantage.

Instead of the straight configuration shown, the glass fiber plate elements 14 and 14' may have a slightly curved shape to the effect that, seen in FIG. 4, element 14 is curved in downward direction and element 14' in upward direction, resulting in a less critical mounting of the diode arrays on the ends of elements 14 and 14'. As elements 14 and 14' are composed of glass fibers, the realisation of the curved shape does not present a problem while the light transmission is not impaired thereby.

To obtain a proper separation of the two images on the strips, such as 8' and 8", of the cathode, an inactive region can be provided between the two CsI strips, which region is fully non-responsive to X-radiation.

I claim:

1. An apparatus for slit radiography, which comprises;
   an X-ray source;
   a slit diaphragm positioned between said X-ray source and a body to be radiographed for forming a substantially planar X-ray beam;
   a filter disposed proximate said slit diaphragm along a longitudinally axis thereof for intercepting a portion of said substantially planar X-ray beam prior to irradiation of said body, said filter blocking relatively low level energy X-ray radiation;
   an elongated X-ray detector tube for collecting radiation passing through said body to be radiographed and extending parallel to said longitudinal axis of said slit diaphragm, said elongated X-ray detector tube including a cathode and an anode extending along said longitudinal axis of said slit diaphragm, said cathode formed with an X-ray detection layer comprised of parallel strips of screening material, one strip of said screening material coinciding with said filter and another strip of said screening material coinciding with an unfiltered portion of said substantially planar X-ray beam; and
   means for providing relative movement between said body to be radiographed and said slit diaphragm and elongated X-ray detector tube, said relative movement being substantially perpendicular to said longitudinal axis of said slit diaphragm.

2. The apparatus for slit radiography as defined in claim 1 wherein said one strip of screening material is of a greater thickness than said another strip of said screening material.

3. The apparatus for slit radiography as defined in claim 1 wherein said filter is formed of copper.

4. The apparatus for slit radiography as defined in claims 1 or 2 wherein said filter is formed of lead.

5. The apparatus for slit radiography as defined in claim 2 wherein said one strip of said screening material of a thickness greater than said another strip of screening material is of greater width than said another strip of screening material.

6. The apparatus for slit radiography as defined in claims 1, 2 or 5 wherein said screening material is CsI.

7. The apparatus for slit radiography as defined in claims 1, 2 or 5 and further including a strip-shaped region of a material non-responsive to X-ray radiation disposed between said strips of screening material.

8. The apparatus of slit radiography as defined in claims 1, 2 or 5 wherein said anode is comprised of strips essentially in registry with said strips of said screening material on said cathode, one of said strips of said anode being provided with a phosphor layer which produces light of a first color and the other of said strips of said anode being provided with a phosphor layer which produces light of a second color.

9. The apparatus for slit radiography as defined in claims 1, 2 or 5 wherein said anode is provided with a phosphor layer on which strips of mutually differing filtering materials are positioned essentially in registry with said strips of said screening material on said cathode.

10. The apparatus for slit radiography as defined in claim 9 wherein said filtering materials are of differing polarization states.

11. The apparatus for slit radiography as defined in claims 1, 2 or 5 wherein said anode is mounted on a face of glass fiber plate facing said cathode, and further including glass fiber elements provided on a face of said glass fiber plate remote from said cathode so as to produce an image on one first strip of screening material to be passed to a first diode array and to produce an image on another strip of screening material to be passed to another diode array.

* * * * *

UNITED STATES PATENT AND TRADEMARK OFFICE
CERTIFICATE OF CORRECTION

PATENT NO. : 4,821,306

DATED : April 11, 1989

INVENTOR(S) : HENDRIK MULDER

It is certified that error appears in the above-identified patent and that said Letters Patent is hereby corrected as shown below:

Figure should read as follows:

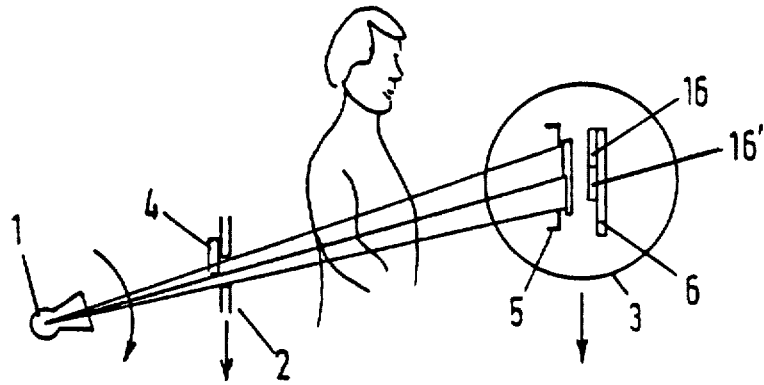

FIG. 1

Signed and Sealed this

Eleventh Day of September, 1990

Attest:

HARRY F. MANBECK, JR.

Attesting Officer     Commissioner of Patents and Trademarks